United States Patent [19]

Vasile et al.

[11] 4,305,294

[45] Dec. 15, 1981

[54] ULTRASONIC APPARATUS AND METHOD FOR MEASURING WALL THICKNESS

[75] Inventors: Carmine F. Vasile, Huntington, N.Y.; Robert B. Thompson, Thousand Oaks, Calif.

[73] Assignee: Rockwell International Corporation, El Segundo, Calif.

[21] Appl. No.: 110,879

[22] Filed: Jan. 10, 1980

[51] Int. Cl.³ .......................................... G01N 29/00
[52] U.S. Cl. ........................................ 73/579; 73/602
[58] Field of Search ........................ 73/579, 602, 643

[56] References Cited

U.S. PATENT DOCUMENTS

| | | | |
|---|---|---|---|
| 3,504,532 | 4/1970 | Muenow et al. | 73/579 |
| 3,996,791 | 12/1976 | Niklas et al. | 73/602 |
| 4,061,017 | 12/1977 | Sloane et al. | 73/579 |

OTHER PUBLICATIONS

Aldridge, Views, Reviews, Previews, (H. Egerton Ed. 1969), pp. 46-57, "Recording Ultrasonic Micrometers".

*Primary Examiner*—Anthony V. Ciarlante
*Attorney, Agent, or Firm*—H. Fredrick Hamann; Craig O. Malin; John J. Deinken

[57] ABSTRACT

Disclosed is a method for determining the thickness of an object, including the steps of generating a higher order mode ultrasonic wave at a first location on the object, varying the frequency of the generated wave, and measuring, at a second location on the object, the minimum frequency at which the generated wave will propagate in the object. Where the ultrasonic wave generated is a horizontally polarized shear wave, the thickness t may be calculated from the relationship $$t = (n\ V_s)/(2 f_c),$$

where:
n is the wave mode number,
$V_s$ is the shear wave velocity, and
$f_c$ is the minimum propagation frequency.

Alternatively, the steps may be repeated for the next consecutive frequency minimum and the thickness t calculated from the formula $$t = V_s/(2\ \Delta f_c)$$

where: $\Delta f_c$ is the difference between two consecutive frequency minima. An apparatus for performing the method includes a transmitting transducer for generating a higher order mode ultrasonic wave at a first location on the object, a signal generator for driving the transmitting transducer with a variable frequency, a receiving transducer for detecting the wave in the object, an amplifier receiving the signal output from the receiving transducer for boosting the signal, and an indicating instrument for receiving the output of the amplifier.

8 Claims, 2 Drawing Figures

ULTRASONIC APPARATUS AND METHOD FOR MEASURING WALL THICKNESS

STATEMENT OF GOVERNMENT INTEREST

The invention herein described was made in the course of or under a contract with the Department of the Air Force.

BACKGROUND OF THE INVENTION

This application is concerned with the field of nondestructive testing and, more particularly, with ultrasonic methods for measuring the thickness of materials.

Nondestructive testing is a branch of materials science which is involved with all aspects of the quality and uniformity of materials. Among the various analytical tools which are available in the discipline of nondestructive tests, ultrasonic techniques have proven useful for a variety of measurement tasks. Ultrasonics may be applied, for example, in the research and development stage to identify material variables. Ultrasonic techniques are also available for use in quality control procedures during the production of an item, and as process control measures to ensure the uniformity of a continuously produced product. Ultrasonic devices and methods may further be employed for the on-site inspection of installed systems and for the examination of in-service components to detect such failure parameters as wear, deterioriation, and corrosion.

A particular area of materials testing in which ultrasonics has proven valuable is in performing material thickness measurements. The thickness of an object may be measured with very high accuracy by ultrasonic techniques. In addition, the use of ultrasonic thickness measurement techniques makes possible the measurement of otherwise unmeasurable components, such as, for example, where physical access to the component is limited so that a direct mechanical measurement cannot be accomplished.

A resonance method for measuring thickness using ultrasonic waves is known in the art. See, e.g., Nondestructive Testing—Views, Reviews, Previews (H. Egerton ed. 1969) at pp. 46-56. In the resonance technique, an ultrasonic wave is generated in the object whose thickness is to be measured, and the frequency of the generated wave is varied until maximum resonance is observed. The thickness of the object is then calculated by correlating the thickness to a multiple of the wavelength of that ultrasonic wave exhibiting maximum resonance. The resonance technique, however, is subject to some shortcomings and disadvantages. The resonant frequency for a particular material or a certain thickness, for example, may be too high to be generated by available ultrasonic transducers. This limitation is particularly applicable in the case of relatively thin plates and tubes. In addition, some transducers, such as the electromagnetic acoustic transducer designs, do not exhibit a sufficiently short response time to operate effectively with the resonance method. Furthermore, the resonance technique will provide a thickness measurement which is limited to a localized area of an object. If a generalized measurement over a broader area of the object, such as a length of tubing, for example, is needed, an area of the object to be tested must be covered with a sequence of resonance measurements at relatively closely spaced surface intervals in order to effectively cover the broader area.

Consequently, a need has developed in the art for an ultrasonic method which is capable of performing an area measurement of thickness.

In addition, a need has developed for an ultrasonic thickness measuring technique capable of measuring the thickness of relatively thin plates and tubes while incorporating the use of electromagnetic acoustic transducers.

Moreover, there is a need in the art for an ultrasonic thickness measuring method which may be utilized to measure an average thickness or to measure a minimum thickness in a preselected area of an object.

SUMMARY OF THE INVENTION

A method for determining the thickness of an object, according to this invention, includes the steps of:

(a) generating a mode of an ultrasonic wave higher than the fundamental mode at a first location on the object, (b) varying the frequency of the generated wave, and (c) measuring, at a second location on the object, the minimum frequency at which the generated wave will propagate in the object.

Where the ultrasonic waves generated are horizontally polarized shear (SH) waves, the thickness t of the object may be calculated from the relationship:

$$t = (nV_s/2f_c)$$

where:
n = the wave mode number (n ≥ 1)
$V_s$ = the shear wave velocity in the object, and
$f_c$ = the minimum propagation frequency.

Alternatively, the thickness t may be calculated by repeating the steps of generating a wave, varying the frequency, and measuring the minimum frequency for the next higher mode wave, and calculating the thickness t of the object from the formula:

$$t = V_s/(2\Delta f_c)$$

where $\Delta f_c$ is the difference in minimum frequency for the two different wave modes.

Examples of the more important features of the invention have been broadly outlined above in order to facilitate an understanding of the detailed description that follows and so that the contributions which this invention provides to the art may be better appreciated. There are, of course, additional features of the invention which will be described below, and which are included in the subject matter of the appended claims.

BRIEF DESCRIPTION OF THE DRAWINGS

Additional objects, features, and advantages of the present invention will become apparent by referring to the detailed description below of the preferred embodiments in connection with the accompanying drawings, wherein like reference numerals refer to like elements throughout all the figures. In the drawings.

DESCRIPTION OF THE PREFERRED EMBODIMENT

Figure 1:
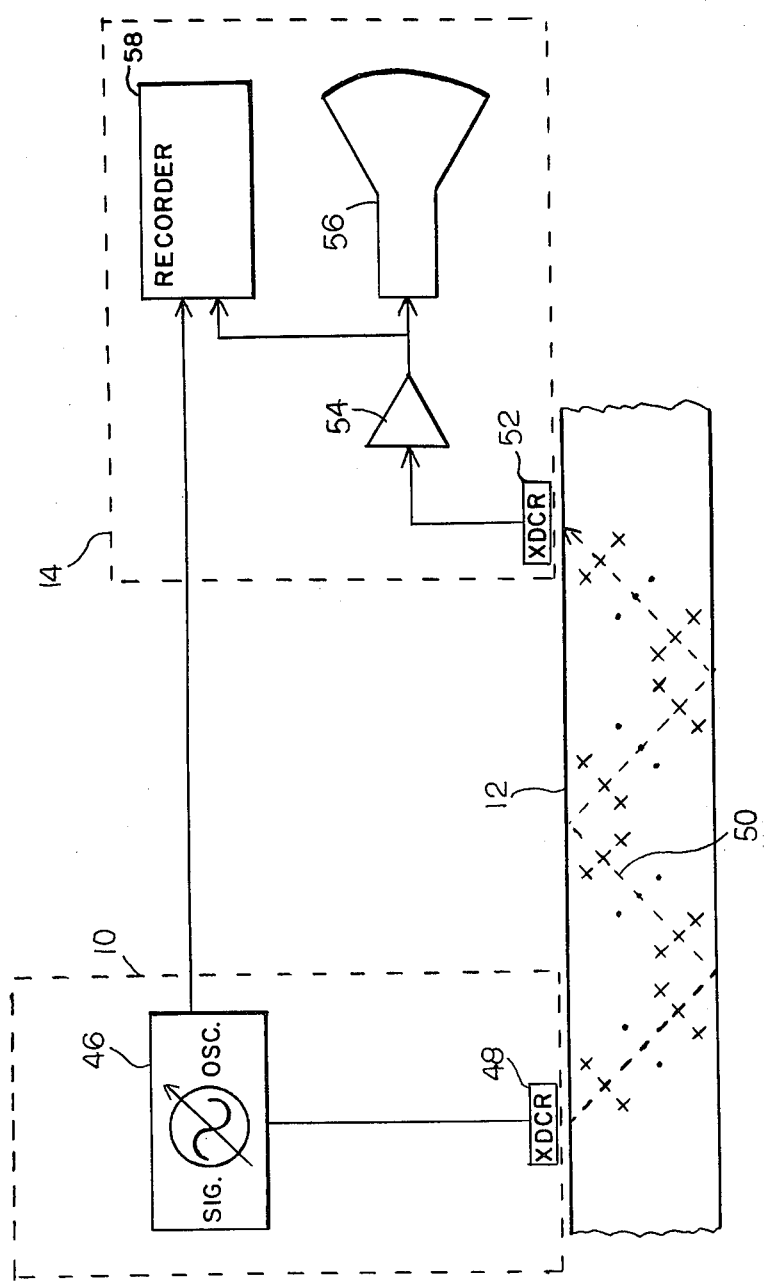
FIG. 1 is a schematic illustration depicting an apparatus constructed according to the invention for measuring the thickness of an object.

Now referring to FIG. 1, a schematic diagram is provided illustrating an ultrasonic thickness measuring apparatus constructed for practicing the present invention. In FIG. 1, the ultrasonic transmitting system 10 generates a variable frequency ultrasonic wave in the wall 12 of an object and the ultrasonic receiving system 14 detects the resulting wave which is propagated through the wall. The minimum frequency at which a wave will propagate can be related to the thickness of the wall, as will be explained in further detail below.

A number of different types of ultrasonic waves, such as longitudinal, horizontally polarized shear (SH), vertically polarized shear (SV), and Lamb waves, can be generated in an elastic material. If the material is bounded on two sides (usually described as a "plate"), horizontal shear (SH) and Lamb waves (which are a combination of vertical shear and longitudinal waves) may be generated. Each type of wave further includes a family of distinct wave modes. In a plate type of material, for example, the fundamental mode SH wave travels in the material without reflecting from the sides of the plate, while higher order mode waves reverberate between the walls of the plate. Because these reflections are characteristic, the higher order mode waves in a plate will each exhibit an abrupt and unambiguous cutoff frequency. If the wave is generated at a frequency lower than the cutoff frequency, that particular mode wave will not propagate in the plate.

Figure 2:
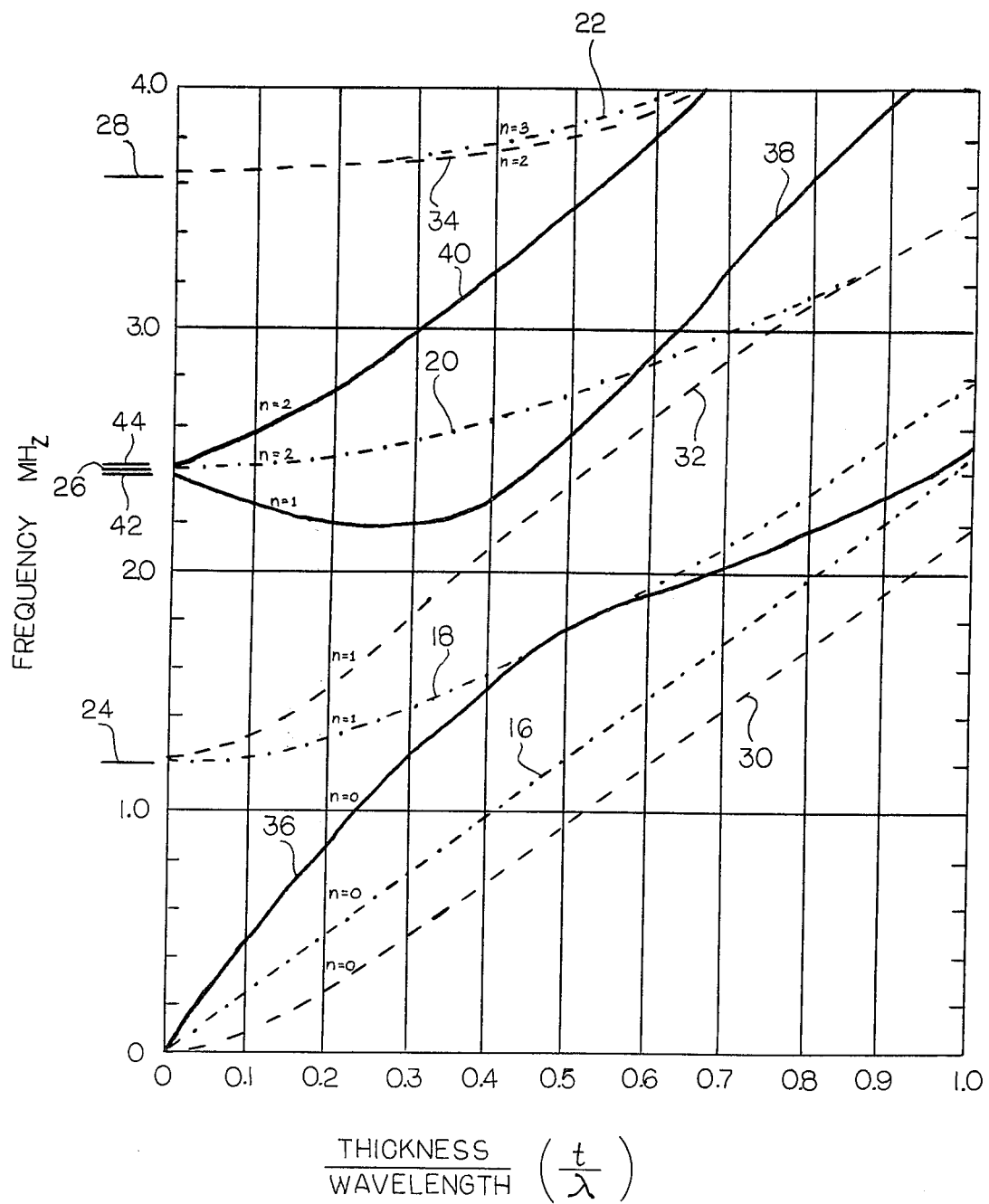
FIG. 2 is a graphical representation illustrating typical dispersion curves for the fundamental and higher order modes of Lamb and horizontal shear ultrasonic waves in a bounded material.

This characteristic of ultrasonic wave propagation in a plate is illustrated in FIG. 2, wherein the dispersion curves are plotted for various modes of a horizontal shear wave, a symmetric Lamb wave, and an antisymmetric Lamb wave travelling in the 0.150 mil thick wall of a 0.875 inch diameter Inconel alloy tube. In FIG. 2, the dotted line 16 corresponds to the fundamental mode (n=0) horizontally polarized shear wave, while dotted lines 18, 20, and 22 correspond to the n=1, 2, and 3 mode horizontal shear waves, respectively. As can be seen from the figure, the minimum frequencies at which the n=1, 2, and 3 mode SH waves will appear are as shown at 24, 26, and 28, respectively. Similarly, the n=0, 1, and 2 modes for antisymmetric Lamb waves are indicated by the dashed lines 30, 32, and 34, respectively. The minimum frequencies for the n=1 and n=2 antisymmetric Lamb waves are as indicated at 24 and 28. Finally, the solid lines 36, 38, and 40 identify the dispersion curves for the n=0, 1, and 2 modes of symmetric Lamb waves. The lines at 42 and 44 denote the minimum frequencies for the symmetric Lamb wave modes n=1 and n=2, respectively.

It is an outstanding feature of this invention to employ the experimentally measured cutoff frequencies for higher order ultrasonic waves to determine the wall thickness of the object in which the waves are propagated. This technique may best be explained by first examining the theory behind wave propagation in an object. For horizontal shear waves, the mathematical relationship between the thickness of the material and a particular minimum or cutoff frequency may be derived by beginning with the general equation for wave motion:

$$\nabla^2 \phi(x,z,t) = \frac{1}{V^2} \frac{\partial^2}{\partial t^2} \phi(x,z,t) \tag{1}$$

where $\phi(x,z,t) = F(x)G(z)e^{j\omega t}$, x is measured in the direction of the thickness of the object, z is measured in the propagation direction, t is time, V is the velocity of the wave, and $\omega$ is the angular frequency of the propagated wave. The wave equation (1) can be solved for the wave number k:

$$k_z = \sqrt{\frac{\omega^2}{V_s^2} - k_x^2}. \tag{2}$$

The cutoff frequency will occur where $k_z = 0$. At that point:

$$\omega^2 / V_s^2 = k_x^2. \tag{3}$$

Imposing the boundary conditions for a plate, $k_x = \pi/t$, equation (3) becomes:

$$\omega_n = (n\pi V_s)/t. \tag{4}$$

In terms of frequency:

$$f_{cn} = (nV_s)/2t \tag{5}$$

Equation (5) relates the cutoff frequency for a particular wave mode horizontal shear wave to the thickness t, the wave mode number n, and the shear wave velocity $V_s$. Although the above derivation is limited to horizontally polarized shear waves, other types of waves, such as Lamb waves, obey similar mathematical relationships. These other relationships, however, are considerably more complex and need not be derived here, although those skilled in the art will appreciate their applicability to the present invention.

Now referring again to FIG. 1, one embodiment of an apparatus for practicing the present invention is illustrated. A variable frequency signal oscillator 46 provides a signal input to a transmitting transducer 48. The transducer 48 is thus motivated to generate a horizontally polarized shear wave, schematically represented at 50, in the wall 12, which is shown in cross section. The representation 50 is not intended to provide an accurate depiction of the actual force distribution of a horizontal shear wave, but merely to indicate that an ultrasonic wave propagates in the wall 12 in the present invention. The frequency of the signal generator 46 is selected to cause one of the higher order mode horizontal shear waves to be generated, as represented by the reverberating wave pattern 50.

The transducer 48 may be of any design suitable for the generation of horizontal shear waves in the proper frequency range. The periodic magnet electromagnetic acoustic transducer is particularly useful for this purpose. Typical designs for such transducers are disclosed in U.S. Pat. No. 4,127,035, the teaching of which is incorporated herein by reference. The period of such a transducer should be selected to approximate the wavelength for the frequency of wave generation which is desired. Although such transducers have a period selected to generate one particular frequency wave, a transducer of finite length will generate waves within a band of frequencies.

The shear wave 50 propagates down the wall 12 and is detected by the receiving transducer 52, which may be of a design similar to the transducer 48. The signal from the transducer 52 is supplied to an amplifier 54, where it is amplified and routed to a suitable indicating device, such as an oscilloscope 56, and to a recorder 58. The oscilloscope 56 provides a visual indication of the amplitude of the propagated wave 50, while the recorder 58 provides a record of the amplitude of the generated wave as a function of the signal generator frequency, thereby providing a means to correlate the cutoff of the propagated wave with the corresponding frequency.

To practice the method of this invention, a higher order mode horizontally polarized shear wave is generated at the location indicated by the transmitting transducer 48 by applying the signal from the signal generator 46 to the transmitter 48. The frequency of the signal generator is then reduced until the shear wave 50 no longer propagates down the wall 12, as indicated by the oscilloscope 56 and the recorder 58. The thickness t of the wall can then be calculated by solving Equation (5) for t:

$$t = (nV_s)/(2f_{cn}). \qquad (6)$$

$V_s$, the velocity of a shear wave in the particular material being tested, can be obtained from a table of such values or, if more accuracy is preferred, can be experimentally measured to the desired accuracy. The wave mode number n can be determined by estimating the approximate thickness of the wall and substituting values for the cutoff frequency, the estimated thickness, and the shear wave velocity in Equation (6) and solving for n. This procedure will yield an approximate value for n from which the true integer value of n can be deduced. Alternatively, experimental measurements may be obtained with different wave modes for two consecutive cutoff frequencies corresponding to n and n+1. As will be apparent to those skilled in the art, Equation (5) can be solved for n and n+1, and the resulting two equations combined to eliminate n and solve for t:

$$t = V_s/2\Delta f_c \qquad (7)$$

where $\Delta f_c$ is the difference between two consecutive frequency minima.

In summary, this invention combines the advantages of traditional ultrasonic resonance thickness measurements, i.e., the potential for very high accuracy and the ability to measure thickness where a part is partially inaccessible, with significant additional features. The invention may be utilized to measure the thickness of very thin plates which heretofore may have been practically unmeasurable by ultrasonic techniques. Furthermore, the technique permits the use of transducers having slower response times. In addition, a measurement may be performed with this invention over a relatively broad area of the part being measured according to the locations selected for generating and receiving the ultrasonic wave. Depending upon the parameters selected and the equipment utilized, the latter feature may be used either to obtain an average thickness measurement over an area or to detect the minimum thickness in a particular area.

In conclusion, although typical embodiments of the present invention have been illustrated and discussed above, numerous modifications and alternative embodiments of the method of this invention will be apparent to those skilled in the art in view of this description. The invention may be of considerable utility, for example, in applications which utilize ultrasonic waves other than horizontal shear waves, such as Lamb waves. Accordingly, this description is to be considered as illustrative only and is provided for the purpose of teaching those skilled in the art the manner of performing the method of this invention. Furthermore, it should be understood that the forms of the invention depicted and described herein are to be considered as the presently preferred embodiments. Various changes may be made in the configuration, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit obtained through reading the above description of the invention.

What is claimed is:

1. A method for determining the thickness of an object, comprising the steps of:
   generating a mode of an ultrasonic wave higher than the fundamental mode at a first location on the object;
   varying the frequency of the generated wave;
   measuring, at a second location on the object, the minimum frequency at which the generated wave will propagate in the object; and
   calculating the thickness of the object by correlating the measured minimum frequency with known parameters of the generated wave.

2. The method of claim 1, wherein the ultrasonic wave generated is a horizontally polarized shear (SH) wave and the thickness t of the object is calculated from the relationship:

$$t = nV_s/2f_c$$

where:
   n = the wave mode number (n ≧ 1),
   $V_s$ = the shear wave velocity in the object, and
   $f_c$ = the minimum propagation frequency.

3. The method of claim 1, wherein the ultrasonic wave generated is a horizontally polarized shear (SH) wave and further comprising the steps of:
   repeating the steps of generating the wave, varying the frequency, and measuring the minimum frequency for the next higher order wave; and
   calculating the thickness t of the object from the formula:

$$t = V_s/(2\Delta f_c)$$

where:
   $V_s$ = the shear wave velocity in the object, and
   $\Delta f_c$ = the difference in minimum frequency for the two different mode waves.

4. The method of claim 1, wherein the object is a substantially flat plate.

5. The method of claim 1, wherein the object is tubular in shape.

6. A method for determining the thickness of an object, comprising the steps of:
- generating a mode of a horizontally polarized shear (SH) wave higher than the fundamental mode at a first location on the object;
- varying the frequency of the shear wave;
- measuring, at a second location on the object, the minimum frequency at which the wave will propagate in the object; and
- calculating the thickness t of the object from the formula:

$$t = nV_s/2f_c$$

where:
n = the wave mode number of the generated wave,
$V_s$ = the shear wave velocity in the object, and
$f_c$ = the minimum propagation frequency.

7. The method of claim 6 wherein the object is tubular in shape and the shear wave establishes a torsional wave in the object.

8. A method for determining the thickness of an object, comprising the steps of:
- generating a mode of a horizontally polarized shear (SH) wave higher than the fundamental mode at a first location on the object;
- varying the frequency of the shear wave;
- measuring, at a second location on the object, the minimum frequency at which the wave will propagate in the object;
- repeating the steps of generating a wave, varying the frequency, and measuring the minimum frequency, for the next higher order wave; and
- calculating the thickness t of the object from the formula $$t = V_s/2\Delta f_c$$

where $V_s$ is the shear wave velocity in the object and $\Delta f_c$ is the difference in minimum frequency for the two different mode waves.

* * * * *